United States Patent [19]
Elias

[11] Patent Number: 5,246,459
[45] Date of Patent: Sep. 21, 1993

[54] MODULAR TIBIAL SUPPORT PEGS FOR THE TIBIAL COMPONENT OF A PROSTHETIC KNEE REPLACEMENT SYSTEM

[76] Inventor: Sarmed G. Elias, 30 E. Huron St., Apt. 3402, Chicago, Ill. 60611

[21] Appl. No.: 840,395

[22] Filed: Feb. 24, 1992

[51] Int. Cl.$^5$ .............................. A61F 2/38; A61F 2/28; A61F 2/30
[52] U.S. Cl. ...................................... 623/20; 623/18; 623/16
[58] Field of Search .................... 623/20, 16, 18, 22; 606/67; 433/172, 174, 173, 175, 176

[56] References Cited

U.S. PATENT DOCUMENTS

| | | | |
|---|---|---|---|
| 3,530,854 | 9/1970 | Kearney | 606/67 |
| 3,892,233 | 7/1975 | Vestby | 606/67 |
| 4,328,593 | 5/1982 | Sutter et al. | 623/18 |
| 4,359,318 | 11/1982 | Gittleman | 433/173 |
| 4,479,271 | 10/1984 | Bolesky et al. | 623/20 |
| 4,645,453 | 2/1987 | Niznik | 433/173 |
| 4,744,755 | 5/1988 | Ross | 433/173 |
| 4,944,757 | 7/1990 | Martinez et al. | 623/20 |
| 5,004,420 | 4/1991 | Soderberg | 433/172 |
| 5,019,103 | 5/1991 | Van Zile et al. | 623/20 |

FOREIGN PATENT DOCUMENTS

| | | | |
|---|---|---|---|
| 0333642 | 9/1989 | European Pat. Off. | 623/20 |
| 0450121 | 10/1991 | European Pat. Off. | 623/20 |
| 0633440 | 12/1982 | Switzerland | 433/172 |

OTHER PUBLICATIONS

Advertising material regarding the Freeman-Samulson Knee (Exhibit A of the Affidavit of Sarmed George Elias).
Advertising material regarding the Kinemax Plus Knee System manufactured by Howmedica (Exhibit B of the Affidavit of Sarmed George Elias).
Advertising material regarding the Genesis Knee System marketed by Smith & Nephew Richards (Exhibit C of the Affidavit of Sarmed George Elias).
Advertising material regarding the Miller-Galante Knee (Exhibit D of the Affidavit of Sarmed George Elias).
Advertising material regarding the PCA Modular Knee System (Exhibit E of the Affidavit of Sarmed George Elias).
Advertising material regarding the Whitesides Knee (Exhibit F of the Affidavit of Sarmed George Elias).

*Primary Examiner*—Randall L. Green
*Assistant Examiner*—Dinh X. Nguyen
*Attorney, Agent, or Firm*—Harness, Dickey & Pierce

[57] ABSTRACT

A modular tibial support peg operable to secure a tibial component of a knee joint prosthesis to a tibia having a groove. The modular tibial support peg includes a cylindrical body with a ridged outer surface operable to engage the groove in the tibia. The modular tibial support peg further includes a plurality of spikes extending inferiorly from the cylindrical body. The spikes are operable to engage the tibia at the inferior end of the groove.

19 Claims, 4 Drawing Sheets

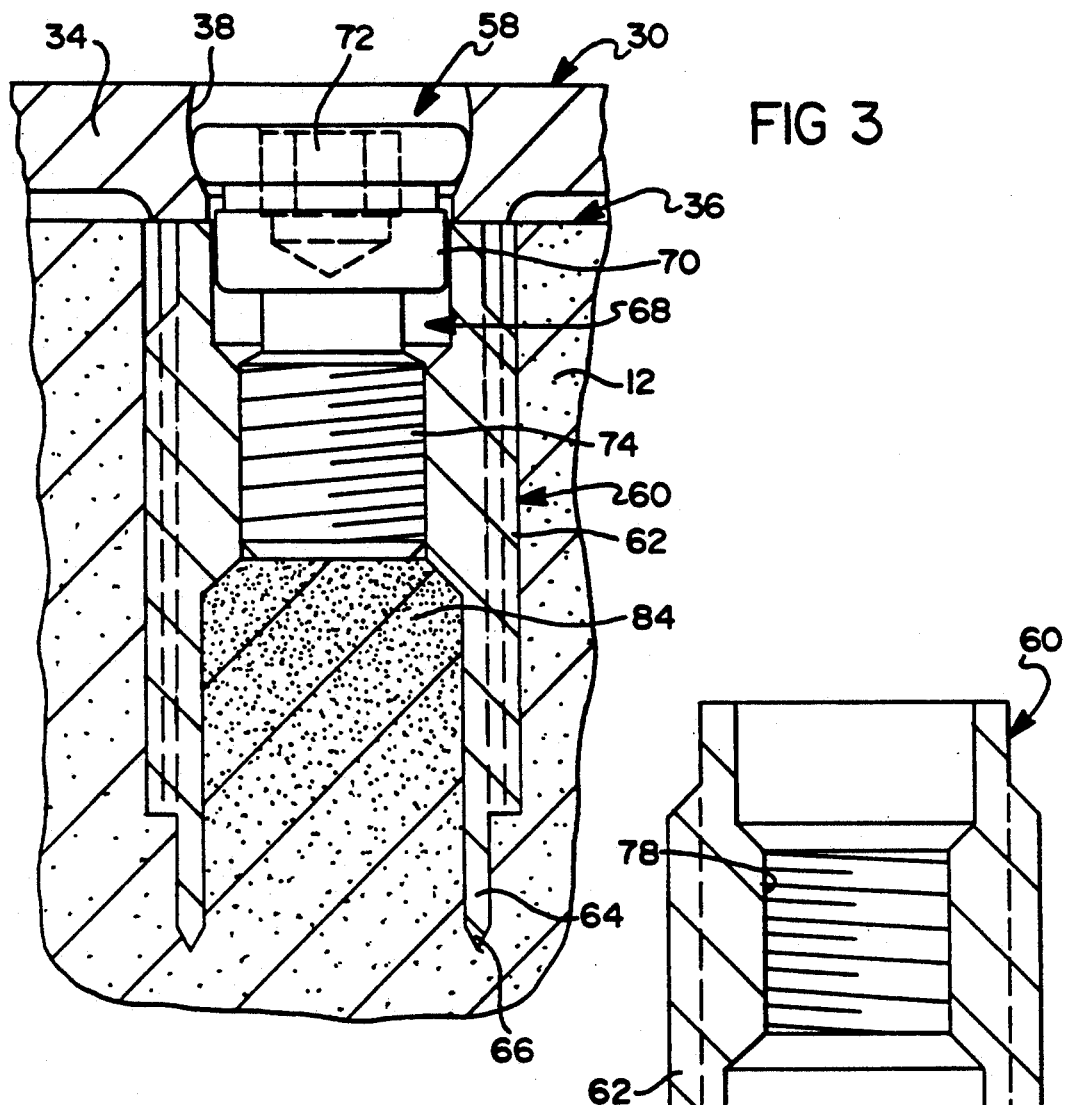
FIG 3
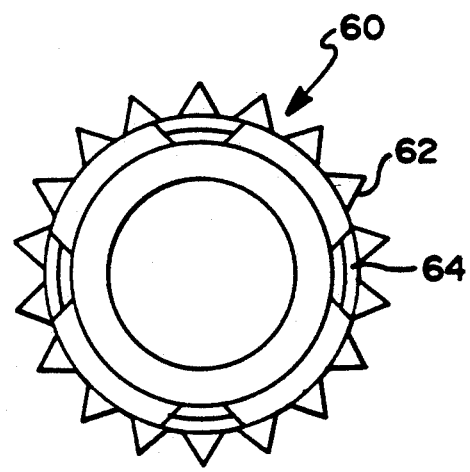
FIG 5
FIG 4

MODULAR TIBIAL SUPPORT PEGS FOR THE TIBIAL COMPONENT OF A PROSTHETIC KNEE REPLACEMENT SYSTEM

BACKGROUND OF THE INVENTION

This invention relates generally to a prosthetic total knee replacement system, and more specifically, to a modular tibial support peg for securing the tibial component of a prosthetic total knee replacement system to a tibia.

The hyaline articular cartilage of a natural knee joint may undergo degenerative changes due to various etiologies. When these degenerative changes are advanced, irreversible and unresponsive to non-operative management, it may ultimately become necessary to replace the natural knee joint with an artificial knee joint prosthetic system.

An artificial knee joint prosthetic system generally includes a femoral component, a tibial component and a patella component. The femoral component is secured to the surgically prepared distal femur and is used to simulate the articulating surface of the natural femur. Similarly, the tibial component is secured to the surgically prepared proximal tibia and is used to simulate the articulating surface of the natural tibia. The tibial component generally includes a tibial insert UHMWP liner, which articulates directly with the femoral component, and a metal backed portion which may include pegs and a tibial stem. This metal backed portion is used to provide secure support to the UHMWP liner as well as provide optimum fixation of the tibial component to the tibia. Finally, the patella component articulates with the patello-femoral groove of the femoral component.

There are several mechanisms which may be used for securing the tibial component to the tibia. Generally, a tubular cavity is formed in the proximal tibia which is used to receive the tibial stem of the metal backed portion of the tibial component. In addition, bone screws may be used which insert through counterbores in the metal backed portion and may extend to the corresponding tibial cortical surfaces. Integral flat or fluted modular solid pegs may also be used to enhance the fixation of the tibial component to the surgically prepared proximal tibia.

SUMMARY OF THE INVENTION

The present invention provides a tibial support peg used in conjunction with an artificial knee joint prosthesis which provides rigid fixation of the metal backed tibial component to the proximal end of a tibia. The invention also provides a surgical procedure for securing the metal backed portion of the tibial component to the tibia by using a modular tibial support peg.

Accordingly, one advantage of the present invention is that the use of a modular tibial support peg as described herein results in a secure fixation of the metal backed portion of the tibial component to the prepared proximal tibia.

Another advantage of the present invention is a method for securing the metal backed portion of the tibial component to the tibia using a modular tibial support peg.

A further advantage of the present invention is a modular tibial support peg of varying lengths which can be used with tibias of varying proximal cortical configurations.

An additional advantage of the present invention is a modular tibial support peg which can be used to accommodate various degrees of metaphyseal bony deficiency in different tibias.

A further advantage of the present invention is a modular tibial support peg which, when implanted, especially in conjunction with bone cement or bone graft to compensate fully for a proximal metaphyseal bony deficiency, either the bone cement or the bone graft will be located in continuity both inside and outside the peg thereby reinforcing the fixation in a strut fashion.

Another advantage of the present invention is a modular tibial support peg which uses a plurality of sharp ridges which facilitate implantation and are embedded in the proximal cancellous end of the tibia thereby enhancing fixation in a press-fit manner.

An additional advantage of the present invention is a modular tibial support peg which preserves bone on the tibia while still providing secure fixation.

Yet another advantage of the present invention is a modular tibial support peg which is used in conjunction with a modular tibial stem of a tibial component to provide adequate fixation between the metal backed portion of the tibial component and the tibia.

The invention, in one form thereof, provides a modular tibial support peg which secures the metal backed portion of a tibial component of a knee joint prosthesis to the proximal tibia with a prepared cylindrical longitudinal groove. The modular tibial support peg includes a cylindrical hollow body having an inner smooth surface and an outer surface with a plurality of sharp ridges to engage the prepared cylindrical longitudinal groove in the tibia. The modular tibial support peg further includes a plurality of spikes extending inferiorly from the cylindrical hollow and sharply ridged body and engages the inferior end of the longitudinal cylindrical groove.

The invention further provides, in another form thereof, a method for securing a metal backed tibial component of a knee joint prosthesis to the proximal tibia. The method comprises initially surgically preparing the proximal tibia in a manner known in the art and then surgically preparing a cylindrical longitudinal groove within the proximal tibia which will come in direct contact with the inner and outer surfaces of the tibial support peg. At least one modular tibial support peg is then attached to the metal backed tibial component and then the metal backed component is then impacted together with the attached tibial stem into the tibia such that the modular tibial support peg engages the longitudinal cylindrical groove in the tibia.

Additional objects, advantages, and features of the present invention will become apparent from the following description and appended claims, taken in conjunction with the accompanying drawings.

BRIEF DESCRIPTION OF THE DRAWINGS

FIG. 3 is a longitudinal sectional view of a modular tibial support peg with impacted cancellous bone in the peg according to the first preferred embodiment of the present invention;

FIG. 4 is a longitudinal sectional view of the cylindrical body of a tibial support peg according to the first preferred embodiment of the present invention;

FIG. 5 is a dimensional view of the cylindrical body of the tibial support peg taken along the lines 5—5 in FIG. 4;

DETAILED DESCRIPTION OF THE PREFERRED EMBODIMENT

The following discussion of the preferred embodiments of a tibial support peg is merely exemplary in nature and is in no way intended to limit the invention or its application or uses.

Figure 1:
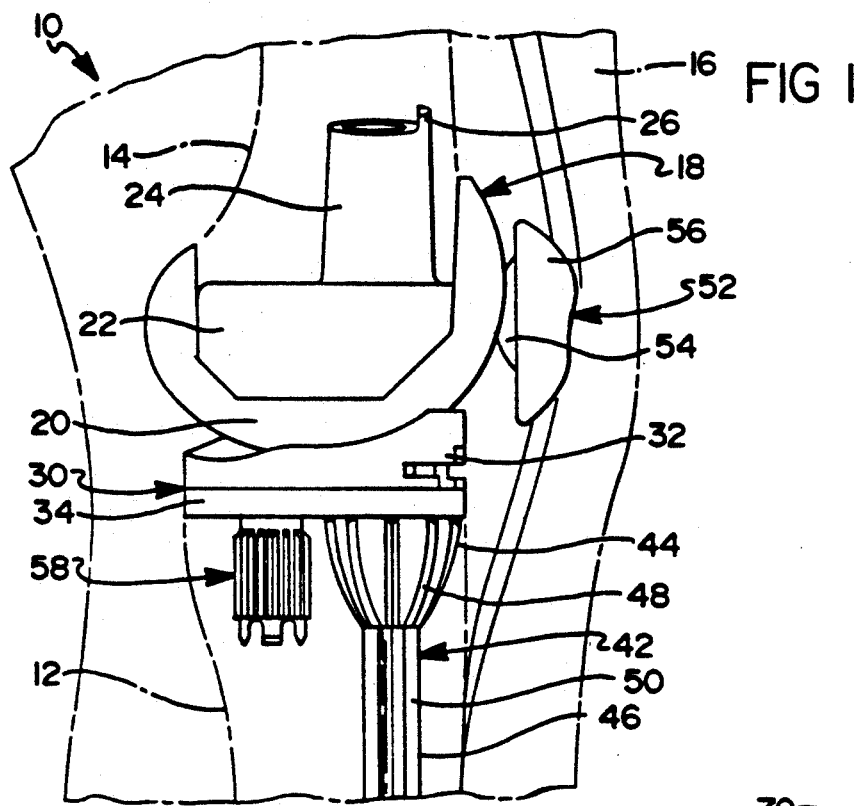
FIG. 1 is an illustration of a sagittally dimensional longitudinal section of a human leg having a knee joint prosthesis with a modular tibial support peg according to the first preferred embodiment of the present invention.
Figure 2:
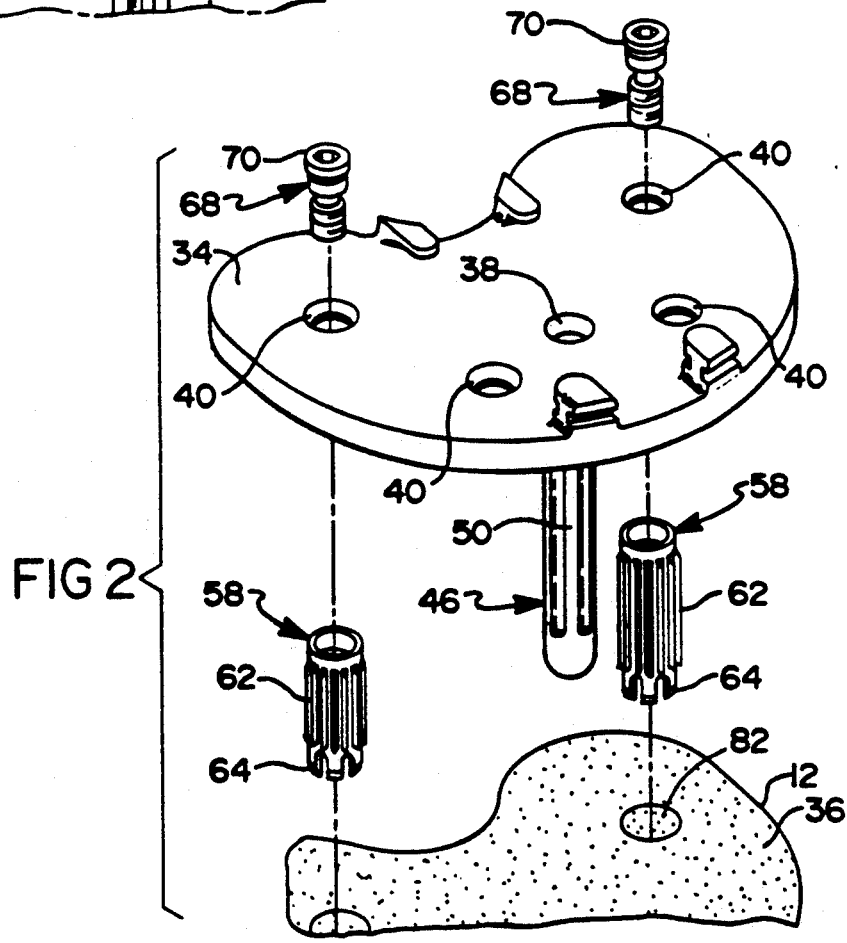
FIG. 2 is an exploded perspective view of a metal backed portion of the tibial component and modular tibial support pegs of varying lengths of the knee joint prosthesis shown in FIG. 1 according to the first preferred embodiment of the present invention.

Referring to FIG. 1, there is shown a total knee joint prosthesis 10 depicted as being functionally secured to a tibia 12 and a femur 14 of a human leg 16. The knee joint prosthesis 10 includes a femoral component 18 which is rigidly fixed to the distal end of the femur 14 after the distal femur 14 has been surgically resected in a manner which is well known in the art. The femoral component 18 includes a condylar portion 20 which engages a tibial component which will be more fully described below. Superiorly adjacent to the condylar portion 20 on the femoral component 18 is an intercondylar portion 22. The intercondylar portion 22 is used to operatively engage a superiorly extending integral member (not shown) on the tibial component so as to limit anteroposterior movement of the femoral component 18.

Connected superiorly to the intercondylar portion 22 of the femoral component 18 is a femoral stem boss 24. The femoral stem boss 24 is used to receive a support member (not shown) which is operable to secure the femoral component 18 to the femur 14. Positioned at a superior 1 end of the femoral stem boss 24 is an anti-rotation member 26. The anti-rotation member 26 engages a recess in the support member so as to prevent rotation of the support member with respect to the femoral component 18. While the femoral component 18 is generally unitary in nature, the present invention may also be used with femoral components of other designs as well. While the femoral component 18 is comprised of a biocompatible high strength alloy such as Ti-4Al-6V, other suitable materials may be used.

The knee joint prosthesis 10 further comprises a tibial component 30 having a tibial insert liner 32 and a metal backed portion 34. The tibial insert liner 32 is operable to articulate with the condylar portion 20 of the femoral component 18. The tibial insert liner 32 is securely placed on the superior surface of the metal backed portion 34 which is used to provide support to the tibial insert liner 32. While the tibial insert liner 32 may be made from ultra-high molecular weight polyethylene (UHMWP), other suitable material may be used.

The metal backed portion 34 of the tibial component 30 is located on the surgically resected proximal tibial 12 and includes an anterior mid-line counterbore 38 as well as a plurality of radially placed counterbores 40. The anterior mid-line counterbore 38 is used to receive a screw that is used for securing a modular tibial stem which is described below. The radially disposed counterbores 40 are used for receiving the tibial bolts of the modular tibial support pegs which is also described below.

To provide first means for securing the metal backed portion of the distal component 34 to the tibia 12, a modular tibial stem 42 is provided. The modular tibial stem 42 extends inferiorly from the metal backed portion 34 into the intramedullary canal of the tibia 12. The modular tibial stem 42 includes a bulbous portion 44 as well as a distal stem portion 46. The bulbous portion 44 of the tibial stem 42 is connected to the inferior surface of the metal backed portion of the tibial component 34, while the distal stem portion 46 of the tibial stem 42 extends inferiorly from the bulbous portion 44. The bulbous portion 44 of the tibial stem 42 includes a plurality of longitudinal sharp ridges 48 while the distal stem portion 46 includes a plurality of longitudinal flutes 50 (preferably four) respectively. The sharp ridges 48, the flutes 50 and the length of the tibial stem 42 assist the tibial component 30 to resist movement between the tibial stem 42 and the tibia 12. While the metal backed portion 34 is made from Ti-6Al-4V, other suitable materials and designs may be used.

The knee joint prosthesis 10 further comprises a patella 52 which includes an artificial patella component 54 as well as a natural patella 56. The artificial patella component 54 is surgically implanted onto or into the natural patella 56 in a manner known in the art and is able to articulate with the corresponding articulating surface of the femoral component 18. While the artificial patella component 54 may be made from UHMWP, other suitable materials may be used.

To provide second means for securing the metal backed portion 34 of the tibial component 30 to the tibia 12, the knee joint prosthesis 10 further comprises a plurality of modular tibial support pegs 58. The modular tibial support pegs 58 are able to be secured to the metal backed portion 34 as well as to the tibia 12 so as to further secure the metal backed portion 34 to the tibia 12. Each of the modular tibial support pegs 58 comprises a cylindrical body 60, the length of which may generally vary depending on the particular patient. For example, if there is a relatively large amount of bone deficiency in the metaphyseal region of the tibia 12 where the modular tibial support peg 58 is to be located, a cylindrical body 60 of relatively greater length may be used. In general, the length of the cylindrical body 60 should be chosen such that the inferior ends of the spikes described below are close to cortical material and as such, the length of the modular tibial support peg 58 will generally correlate with the proximal tibial cortical configuration.

The cylindrical body 60 includes a plurality of sharp ridges 62 extending longitudinally along an outer surface of the cylindrical body 60. The sharp ridges 62 are operable to be at least partially driven into the cancellous walls of a longitudinal cylindrical groove formed in the tibia 12 for receiving the modular tibial support peg 58 so as to enhance the fixation of the cylindrical body 60 to the tibia 12 as more fully described below. Located at the distal end of the cylindrical body 60 is a plurality of spikes 64 (preferably 4). The spikes 64 extend inferiorly from the cylindrical body 60 and if required, engage the sclerotic bone located on the surface of the tibial bony deficiency. Furthermore, the spikes 64 are generally polished and include tapered distal ends 66 to facilitate insertion into the cancellous bone of the tibia 12 in the first preferred embodiment of the present invention.

To provide means for securing the modular tibial support peg 58 to the metal backed portion 34, each of the tibial support pegs 58 further comprises a tibial bolt 68. The tibial bolt 68 is operable to be partially inserted through one of the radially placed counterbores 40 in the metal backed portion 34 and then threadably engage the cylindrical body 60 thereby securing the cylindrical body 60 to the metal backed portion 34. The tibial bolt 68 includes a toroidal head portion 70 at its superior end which is operable to seat within the radially placed counterbores 40 of the metal backed portion 34. Located within the toroidal head portion 70 is a hexed cavity 72 which is able to provide a locking engagement with an appropriate tool so as to allow rotation of the tibial bolt 68 upon rotation of the tool. Extending inferiorly from the head portion 70 of the tibial bolt 68 is a threaded portion 74. The threaded portion 74 is operable to threadably engage the internal threaded bore 78 of the modular tibial support peg 58. Accordingly, the modular tibial support peg 58 may be secured to the metal backed portion 34 by inserting the tibial bolt 68 through one of the radially placed counterbores 40 and then causing engagement between the threaded portion 74 of the tibial bolt 68 and the cylindrical body 60.

While the modular tibial support pegs 58 may be secured to any of the radially placed counterbores 40, it is preferable to secure two of the modular tibial support pegs 58 to two of the counterbores 40 which are located on the posterior part of the metal backed portion 34. By securing the modular tibial support pegs 58 to the two posterior most counterbores 40 on the metal backed portion 34, a relatively secure triad arrangement is formed between the tibial support pegs 58, the tibial stem 42 and the surgically prepared proximal tibia 12. While the tibial support pegs 58 and the tibial bolts 80 are made of a titanium alloy such as Ti-4Al-6V, suitable other materials may be used.

Figure 7A:
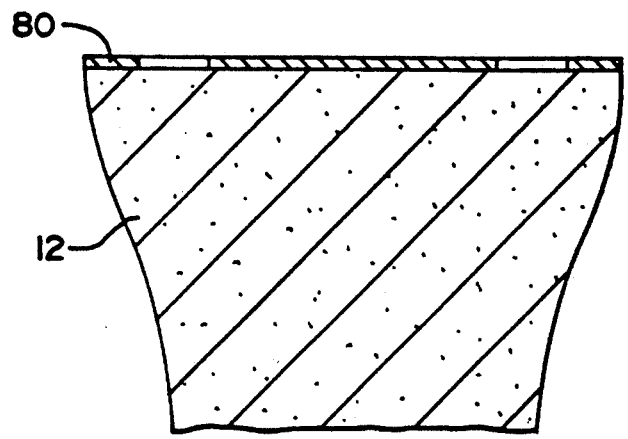
FIGS. 7(A)–7(C) are illustrations showing the surgical procedure for securing a metal backed portion of the tibial component to a tibia using the modular tibial support pegs according to the first preferred embodiment of the present invention.
Figure 7B:
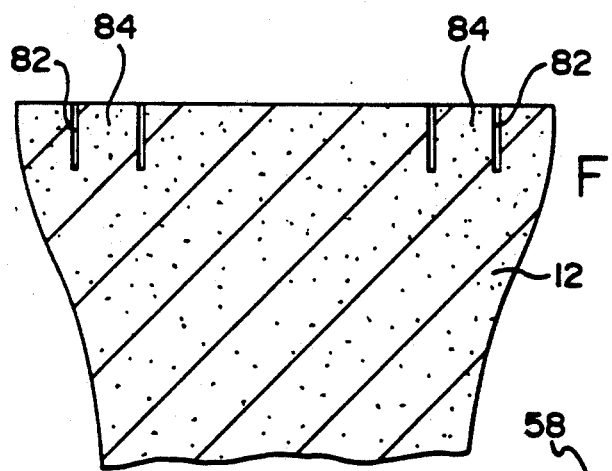

Now turning to FIGS. 7(A)–7(C), the method for securing the metal backed portion 34 to the tibia 12 using the modular tibial support pegs 58 will now be described. Once the tibia plateau 36 is surgically resected so as to form, if applicable, a relatively flat tibial surface, the surgeon determines the size of the metal backed portion 34 which will most closely match the size of the resected proximal tibial 12 with the aid of a tibial template 80. The surgeon then, after selecting a tibial template 80 which corresponds to the size of the metal backed portion 34, temporarily attaches the template 80 to the surgically resected proximal tibia 12. The tibial template 80 allows the surgeon to position the various reamers in the correct position on the tibia 12 so as to form the various cavities described below.

The surgeon then reams the tubular cavity 81 (see FIG. 12) for accepting the tibial stem 42 to the desired depth. After the tubular cavity 81 has been formed, the surgeon measures the desired depth of the longitudinal cylindrical grooves 82 which are to eventually receive the modular tibial support pegs 58. One method of measuring this depth is by drilling a small hole in the region of the tibia 12 through the radially placed holes 40 on the selected tibial template 80 proximate to where the longitudinal cylindrical grooves 82 are to be formed until the drill bit impinges the corresponding cortex of the tibia 12. The depth of this hole is then measured so as to allow the surgeon to determine the desired depth to which the longitudinal cylindrical grooves 82 are to be prepared.

The surgeon then uses a hole saw (not shown) to form a longitudinal cylindrical groove 82 to the desired depth. The use of a hole saw permits most of the bone material within the longitudinal cylindrical grooves 82 to be retained so as to form a column 84 of bone which provides additional support for the modular tibial support peg 58. When the longitudinal cylindrical grooves 82 are prepared in this manner, the bone material within the column 84 will be located in the interior of the cylindrical body 60 of the tibial support peg 58.

The outer diameter of the longitudinal cylindrical grooves 82 are selected such that the plurality of sharp ridges 62 of the cylindrical body 60 will be at least partially embedded laterally into the cancellous bone walls of the longitudinal cylindrical grooves 82 in a press-fit manner.

The tibial bolts 68 are then inserted partially through preferably the posterior-most counterbores 40 in the metal backed portion 34 and then threaded into the threaded bore 78 of the cylindrical body 60 so as to rigidly secure the modular tibial support pegs 58 to the metal backed portion 34. The metal backed portion 34 is then impacted onto the tibia 12 thereby driving the modular tibial support pegs 58 into the longitudinal cylindrical grooves 82 and the tibial stem 42 into the tubular cavity 81. It will be noted that the modular tibial support pegs 58 can be secured to the tibia 12 with or without the use of bone cement. However, if bone cement is used the surgeon should apply bone cement to the superior surface 36 of the proximal tibia 12 and may avoid applying cement in the cylindrical longitudinal groove 82, on the column of bone 84 and the tubular cavity 81.

Figure 6:
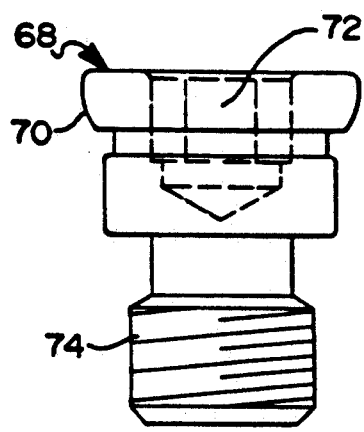
FIG. 6 is a dimensional view of a tibial bolt of a tibial support peg according to the first preferred embodiment of the present invention.
Figure 8:
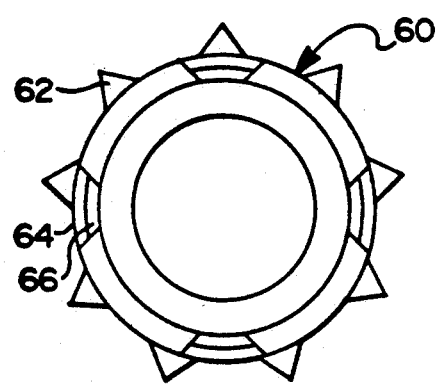
FIG. 8 is a dimensional view of the modular tibial support peg taken along the line 5—5 according to the second preferred embodiment of the present invention.
Figure 9:
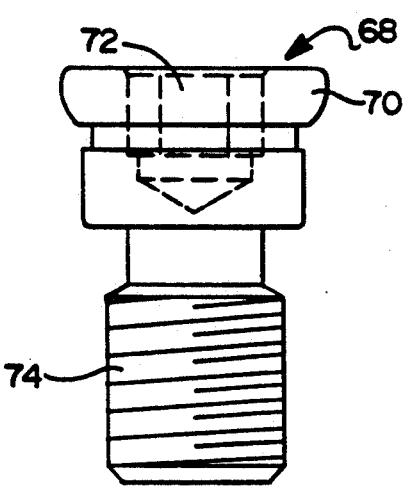
FIG. 9 is a dimensional view of a tibial bolt of a tibial support peg according to the second preferred embodiment of the present invention.

The modular tibial support pegs 58 of the present invention may be of different configurations. As shown in FIG. 8, the tibial support peg 58 of the second preferred embodiment of the present invention includes nine sharp ridges 62 as opposed to eighteen as shown with the tibial support peg 58 of the first embodiment shown in FIG. 5. It will be appreciated that any other suitable number of appropriately spaced sharp ridges 62 may be used. As shown in FIG. 9, the tibial bolt 68 may be of differing length when compared to the tibial bolt 68 shown in FIG. 6 so as to accommodate the cylindrical body 60 of different lengths.

Figure 7C:
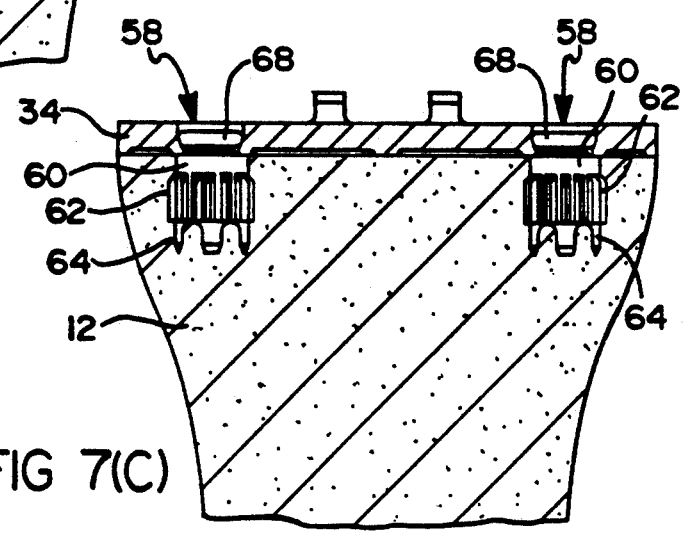
Figure 10:
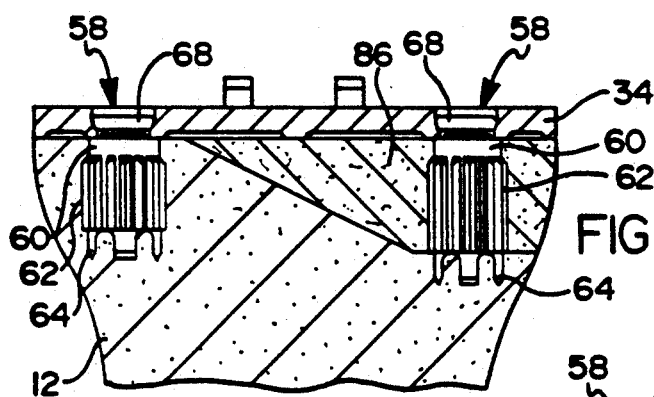
FIG. 10 is a coronally dimensional longitudinal sectional view of a proximal tibia having a region with bone deficiency and incorporating a modular tibial support peg and either bone cement or bone graft and in either combination, compensating fully for the bony defect according to the first preferred embodiment of the present invention.

Now turning to FIG. 10, a coronally dimensional and longitudinal sectional view of the tibia 12 is shown which is similar to the view shown in FIG. 7(C). However, the tibia 12 in this view includes a region 86 having a metaphyseal bony deficiency. For the region 86 in the tibia 12 which is subject to this deficiency, a modular tibial support peg 58 can be used which includes a longer cylindrical body 60 such that the spikes 64 are rigidly secured in the tibial bone material which may or may not be sclerotic. When the tibial support pegs 58 are implanted in this manner, the region 86 of bone deficiency is preferably filled with bone cement or a bone graft and in continuity with same inside the modular tibial support peg in a manner known in the art.

Figure 11:
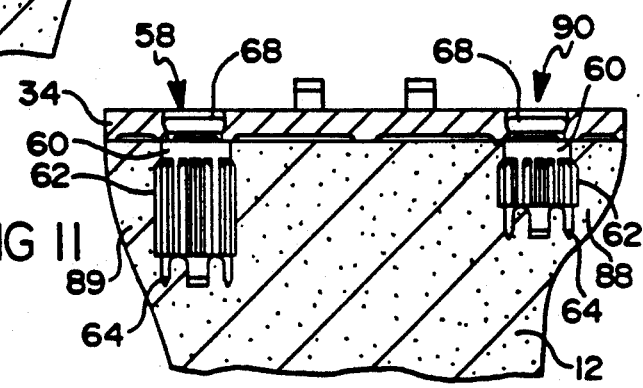
FIG. 11 is a coronally dimensional longitudinal sectional view of a proximal tibia having a variable medial-lateral cortical configuration and incorporating two modular tibial support pegs of different sizes according to the first preferred embodiment of the present invention.

FIG. 11 reveals the suitability of the modular tibial support pegs 58 for use with a tibia 12 having a normally variant proximal tibial cortical configuration. The tibia 12 is shown which has a medial portion 88 having a cortical configuration different from the cortical configuration of the lateral portion 89. Accordingly, a shorter modular tibial support peg 90 would normally be implanted within the medial portion 88 so as to accommodate this normal anatomical configuration.

Figure 12:
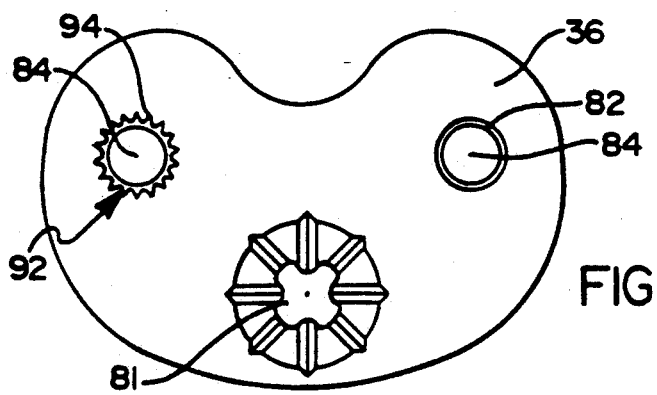
FIG. 12 is a superior view of a tibia depicting the different longitudinal cylindrical groove imprints which are prepared for accepting the tibial support pegs according to the first preferred embodiment of the present invention, as well as the bony cancellous imprint of the tibial stem.

Now turning to FIG. 12, a superior view of the resected proximal tibial 12 which illustrates a combination of bony imprints of the under surface support component of the metal backed portion 34 together the cylindrical longitudinal groove 82. The cavity 81 for accepting the tibial stem 42 is shown extending distally into the tibia 12 at an anterior mid-line location from the medial-lateral plane. In addition, the longitudinal cylindrical groove 82 for receiving the modular tibial support peg 58 is shown after the cut has been made by the hole saw. Finally, an imprint cavity 92 illustrates the imprint of a tibial support peg 58 as it would appear if the modular tibial support peg 58 were inserted into a longitudinal cylindrical groove 82 and removed. As is apparent, the imprint cavity 92 includes a series of longitudinally extending ribs 94 in the walls of the imprint cavity 92 which were formed by the sharp ridges 62. Two imprint cavities 92 are formed with two modular tibial support pegs 58 differing only in length.

The foregoing discussion discloses and describes merely exemplary embodiments of the present invention. For example, it will be appreciated that porous material or hydroxy apatite may be applied to the modular tibial support peg alone or in combination to promote biological ingrowth. One skilled in the art will readily recognize from such discussion, and from the accompanying drawings and claims, that various changes, modification and variations can be made therein without departing from the spirit and scope of the invention.

What is claimed is:

1. In combination, a tibial support peg for securing a tibial component of a knee joint prosthesis to a tibia having a groove with an inferior end, said tibial component including
    a backing portion,
    a tibial stem extending from said backing portion, said tibial stem having a bulbous portion and a fluted stem portion, said fluted stem portion extending inferiorly from said bulbous portion, said tibial support peg comprising:
    a cylindrical body extending from said backing portion, said cylindrical body engageable with said groove in said tibia; and
    a plurality of spikes extending inferiorly from the cylindrical body, said spikes being engageable with said tibia at said inferior end of said groove, said cylindrical body and said plurality of spikes of said tibial support peg cooperating with said tibial stem to secure said tibial component to said tibia.

2. The tibial support peg according to claim 1, wherein said cylindrical body has a length selected to accommodate for bone deficiencies in said tibia.

3. The tibial support peg of claim 1, wherein said cylindrical body includes an inner surface which receives a portion of said tibia when said cylindrical body engages said groove in said tibia.

4. The tibial support peg according to claim 1, wherein the cylindrical body includes an outer surface having a plurality of longitudinally extending ridges, said plurality of longitudinally extending ridges engageable with said groove.

5. The tibial support peg according to claim 1, wherein said plurality of spikes have tapered end portions to facilitate insertion of said cylindrical body into said groove.

6. The tibial support peg according to claim 1, wherein said cylindrical body includes an inner surface which receives bone graft when said cylindrical body engages said groove in said tibia.

7. The tibial support peg according to claim 1, wherein said cylindrical body has an inner surface which receives bone cement.

8. In combination, a modular tibial support peg for securing a tibial component of a knee joint prosthesis to a tibia having a groove with an inferior end, said tibial component including
    a backing portion,
    a tibial stem extending from said backing portion, said tibial stem having a bulbous portion and a fluted stem portion, said fluted stem portion extending inferiorly from said bulbous portion, said modular tibial support peg comprising:
    a cylindrical body extending from said backing portion and being engageable within said groove of said tibia, said cylindrical body having an outer surface with a plurality of longitudinally extending ridges disposed thereon; and
    a tibial bolt engaging said tibial component at a first end and said cylindrical body at a second end, said cylindrical body of said modular tibial support peg cooperating with said tibial stem to secure said tibial component to said tibia.

9. The modular tibial support peg of claim 8, wherein said tibia has an anatomical configuration and said cylindrical body has a length, said length of said cylindrical body accommodates said anatomical configuration of said tibia.

10. The modular tibial support peg of claim 8, wherein said cylindrical body is hollow and has an inner surface which receives a column of bone defined by said groove.

11. The modular tibial support peg according to claim 10, wherein said tibial bolt includes a toroidal head portion engageable with a counterbore in said tibial component.

12. The modular tibial support peg according to claim 11, wherein said cylindrical body includes a plurality of spikes which extend inferiorly from said cylindrical body, said plurality of spikes engageable with said tibia at said inferior end of said groove.

13. The modular tibial support peg according to claim 12, wherein said cylindrical body has a length which accommodates for bone deficiencies in said tibia.

14. A method for securing a tibial component of a knee joint prosthesis to a tibia, said tibial component having a metal backed portion, said method comprising the steps of:

provm a tibial support peg including a cylindrical body having an inner surface and an outer surface;

providing a tibial stem extending from said metal backed portion, said tibial stem having a bulbous portion and a fluted stem portion, said fluted stem portion extending inferiorly from said bulbous portion;

preparing said tibia for receiving said tibial component including forming a longitudinal cylindrical groove in said tibia for receiving said tibial support peg and forming a cavity in said tibia for receiving said tibial stem;

insert a tibial bolt having a distal end partially through a bore formed in said metal backed portion such that said distal end of said tibial bolt engages said inner surface of said cylindrical body, said tibial bolt having a head portion operable to engage said bore of said metal backed portion to allow said cylindrical body to extend from said metal backed portion;

inserting said tibial stem into said cavity;

inserting said tibial support peg into said longitudinal cylindrical groove such that said outer surface of said tibial support peg engages said longitudinal cylindrical groove; and allowing said tibial support peg and said tibial stem to cooperate to secure said tibial component to said tibia.

15. The method according to claim 14, wherein said step of providing a tibial support peg includes the step of forming a plurality of spikes on said cylindrical body, said step of inserting said tibial support peg into said longitudinal cylindrical groove further includes the step of embedding said spikes into said tibia.

16. The method according to claim 15, wherein said step of providing a tibial support peg includes the step of forming a plurality of longitudinally extending ridges along the outer surface of said cylindrical body, the step of inserting said tibial support peg into said longitudinal cylindrical groove further includes the step of driving said longitudinally extending ridges into said wall of said longitudinal cylindrical groove.

17. The method according to claim 16, wherein the step of preparing said tibia for receiving said metal backed portion includes the steps of drilling a hole in said tibia until cortical material is reached;

measuring the depth of said hole; and selecting the length of said tibial support peg .-which approximately corresponds to the depth of said hole.

18. The method according to claim 17, wherein said step of preparing said tibia for receiving said metal backed portion includes the step of using a hole saw to form said longitudinal cylindrical groove.

19. The method according to claim 18, wherein the step of inserting said tibial support peg into said longitudinal cylindrical groove includes the step of causing a portion of said tibia to be disposed within said inner surface of said tibial support peg.

* * * * *

UNITED STATES PATENT AND TRADEMARK OFFICE
CERTIFICATE OF CORRECTION

PATENT NO.   : 5,246,459
DATED        : September 21, 1993
INVENTOR(S)  : Sarmed G. Elias It is certified that error appears in the above-indentified patent and that said Letters Patent is hereby corrected as shown below:

Column 4, line 3, delete "1".

Column 7, line 34, after "together" insert --with--.

Column 7, line 53, "hydroxy apatite" should be --hydroxyapatite--.

Column 7, line 58, "modification" should be --modifications--.

Column 9, line 27, Claim 14, "insert" should be --inserting--.

Column 10, line 26, Claim 17, after "peg" delete ".-".

Signed and Sealed this

Thirtieth Day of August, 1994

Attest:

BRUCE LEHMAN

*Attesting Officer*    *Commissioner of Patents and Trademarks*